United States Patent [19]

Shimizu et al.

[11] Patent Number: 4,604,493

[45] Date of Patent: Aug. 5, 1986

[54] 1-CYCLOHEXYL-1,4-DIMETHYL DECAHYDRONAPHTHALENE AND A WORKING FLUID FOR TRACTION DRIVE FORMULATED THEREWITH

[75] Inventors: Nobuaki Shimizu; Toshiyuki Tsubouchi, both of Sodegaura; Hitoshi Hata, Ichihara, all of Japan

[73] Assignee: Idemitsu Kosan Company Limited, Tokyo, Japan

[21] Appl. No.: 785,457

[22] Filed: Oct. 8, 1985

[30] Foreign Application Priority Data

Oct. 18, 1984 [JP] Japan ................................ 59-218892

[51] Int. Cl.$^4$ ............................................. C07C 13/50
[52] U.S. Cl. ................................... 585/360; 208/14; 252/73; 585/20; 585/21; 585/22; 585/269; 585/270; 585/516

[58] Field of Search ...................... 208/14; 252/9, 73; 585/20, 21, 22, 23, 360, 361, 516, 269, 270

[56] References Cited

U.S. PATENT DOCUMENTS

| | | | |
|---|---|---|---|
| 4,521,324 | 6/1985 | Tsubouchi et al. | 585/360 |
| 4,525,290 | 6/1985 | Tsubouchi et al. | 585/360 |
| 4,556,503 | 12/1985 | Tsubouchi et al. | 585/360 |

Primary Examiner—Andrew H. Metz
Assistant Examiner—A. Pal
Attorney, Agent, or Firm—Frishauf, Holtz, Goodman & Woodward

[57] ABSTRACT

The invention provides a novel compound 1-cyclohexyl-1,4-dimethyl decahydronaphthalene which is useful as fluids for traction drive. The compound can be synthesized by the hydrogenation of 1,4-dimethyl-4-phenyl-1,2,3,4-tetrahydronaphthalene and analytical results for the identification of the compound are given.

3 Claims, 3 Drawing Figures

1-CYCLOHEXYL-1,4-DIMETHYL DECAHYDRONAPHTHALENE AND A WORKING FLUID FOR TRACTION DRIVE FORMULATED THEREWITH

BACKGROUND OF THE INVENTION

The present invention relates to a novel compound 1-cyclohexyl-1,4-dimethyl decahydronaphthalene and a working fluid for traction drive formulated therewith, and more particularly, to 1-cyclohexyl-1,4-dimethyl decahydronaphthalene which is a novel compound suitable as a principal ingredient of working fluids for traction drive or other uses as well as a working fluid for traction drive formulated with this compound.

Generally speaking, a working fluid for traction drive is a fluid used in apparatuses of traction drive, i.e. friction drive apparatuses by rolling contact, such as a continuously variable transmission, and the like. When a fluid for traction drive is used in a high-performance traction drive apparatus, the fluid is required to have a high traction coefficient and stability against heat and oxidation along with inexpensiveness as a matter of course.

In recent years, various types of compounds have been proposed as a fluid for traction drive including various polycyclic naphthenic compounds such as those disclosed in Japanese Patent Publications 338/1971, 339/1971, 35763/1972, 42067/1973, 42068/1973 and 36105/1978 and Japanese Patent Kokai 43108/1980 and 40726/1980.

These compounds, however, have a relatively high viscosity and cannot be free from the problems of a low efficiency of power transmission due to agitation loss and a limitation in the serviceable range of temperature due to the large temperature dependency of the traction coefficient. Moreover, conventional compounds are not satisfactory for the purpose since a fluid for traction drive is sometimes used at a high temperature of up to 120 to 140° C.

SUMMARY OF THE INVENTION

A primary object of the present invention is therefore to provide a novel and improved fluid for traction drive free from the above described problems and disadvantages in the conventional fluids for traction drive in the prior art.

Another object of the invention is to provide a novel compound which is useful as a principal ingredient of a fluid for traction drive mentioned above.

Thus, the compound of the present invention, which is a novel compound not known or not described in any prior art literatures and suitable as the principal ingredient of a fluid for traction drive, is 1-cyclohexyl-1,4-dimethyl decahydronaphthalene expressed by the structural formula

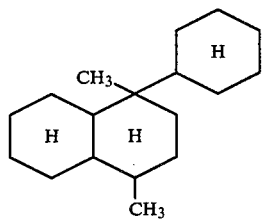
(I)

Accordingly, the fluid for traction drive provided by the present invention comprises 1-cyclohexyl-1,4-dimethyl decahydronaphthalene expressed by the above given structural formula (I).

DETAILED DESCRIPTION OF THE PREFERRED EMBODIMENTS

Figure 1:
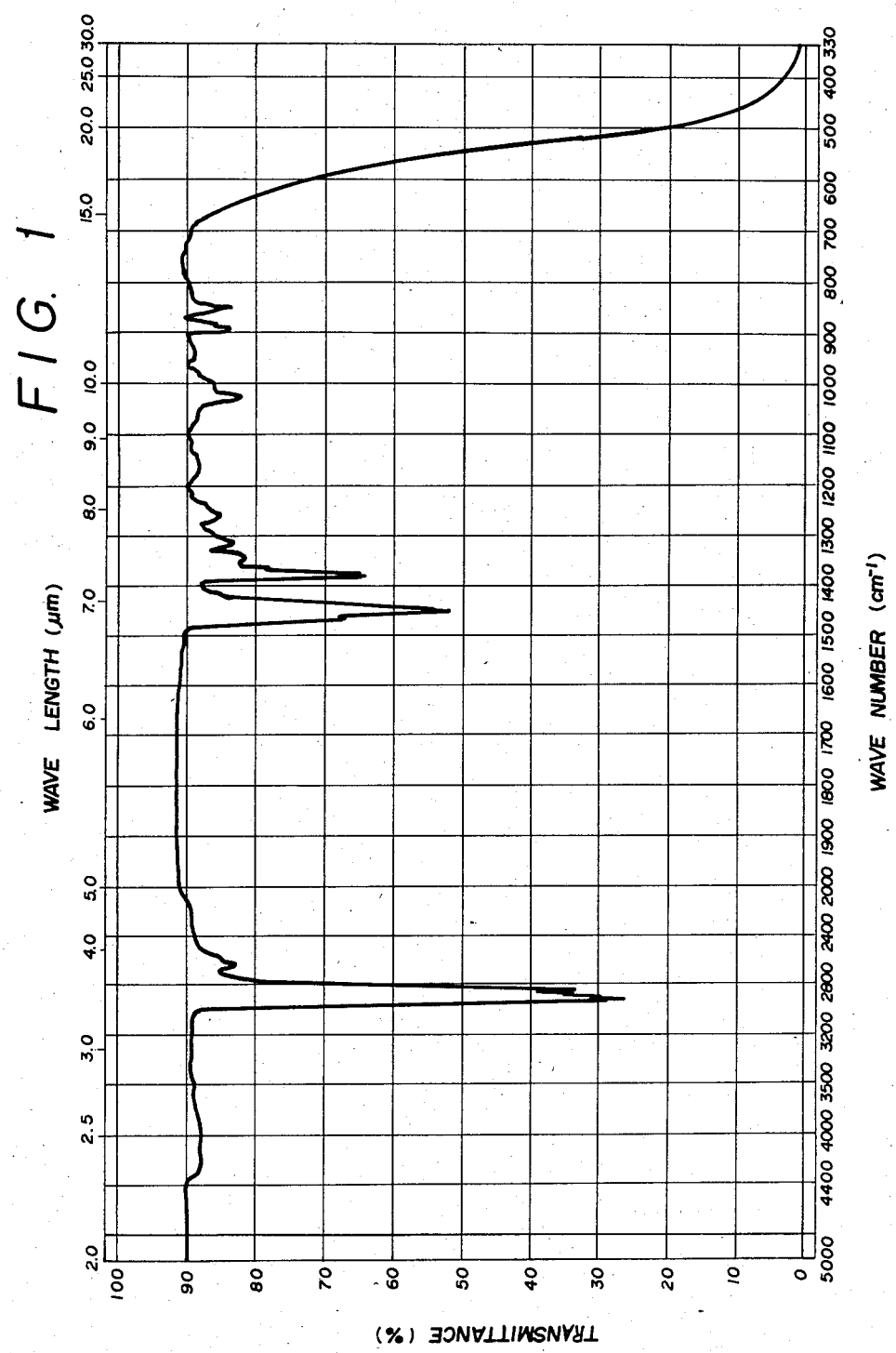
FIG. 1 is an infrared absorption spectrum of 1-cyclohexyl-1,4-dimethyl decahydronaphthalene prepared in Example 1.

The novel compound of the invention discovered as a result of the extensive investigations by the inventors to obtain a fluid for traction drive as mentioned above is 1-cyclohexyl-1,4-dimethyl decahydronaphthalene which is a compound obtained by the hydrogenation of 1,4-dimethyl-4-phenyl-1,2,3,4-tetrahydronaphthalene which in turn is a dimerization product of α-methylstyrene.

1-Cyclohexyl-1,4-dimethyl decahydronaphthalene as the inventive compound of the structural formula (I) can be synthesized in various synthetic routes, of which the above mentioned method by the hydrogenation of 1,4-dimethyl-4-phenyl-1,2,3,4-tetrahydronaphthalene is the most convenient and efficient. Thus, α-methylstyrene is subjected to a dimerization reaction in tert-butyl alcohol in the presence of potassium tert-butoxide as a catalyst to give 1,4-dimethyl-1,4-phenyl-1,2,3,4-tetrahydronaphthalene. This reaction is expressed by the following reaction equation:

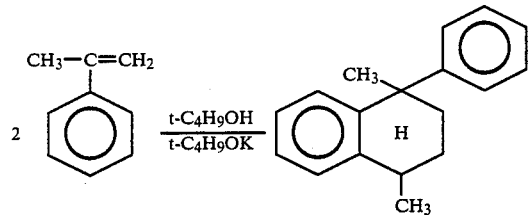

The thus obtained 1,4-dimethyl-4-phenyl-1,2,3,4-tetrahydronaphthalene is then hydrogenated in the presence of a catalyst to give the desired 1-cyclohexyl-1,4-dimethyl decahydronaphthalene. This reaction of hydrogenation is expressed by the following reaction equation:

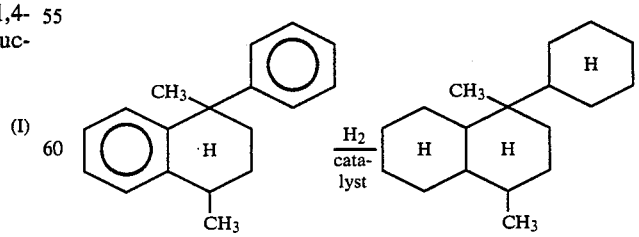

The conditions for the hydrogenation reaction are not particularly limitative although the reaction is performed usually in the presence of a catalyst containing an active ingredient such as nickel, platinum, palladium, ruthenium, rhodium, iridium and the like at a temperature in the range from 20° to 250° C. and under a pressure in the range from 5 to 10 atmospheres. The reaction can be performed either in an organic solvent or in a solvent-free condition.

1-Cyclohexyl-1,4-dimethyl decahydronaphthalene obtained in this manner is a novel compound and, as is mentioned above, useful as a fluid for traction drive. This compound is chemically stable and odorless so that it is also useful as a high-boiling solvent and in many applications as a synthetic functional fluid such as working fluids, lubricant oils and the like.

In the following, the present invention is described in more detail by way of examples.

PREPARATION

Into a four-necked glass flask of 1-liter capacity equipped with a stirrer, reflux condenser with a calcium chloride tube, thermometer and gas inlet tube were introduced 591 g (5 moles) of α-methylstyrene, 2.8 g (0.05 mole) of potassium tert-butoxide and 3.7 g (0.05 mole) of tert-butyl alcohol to form a reaction mixture which was heated at 149° C. for 22 hours under agitation while argon gas was continuously introduced into the flask at a rate of 10 ml/minute through the gas inlet tube. After cooling of the reaction mixture following the above reaction time, introduction of argon gas was discontinued and the reaction mixture transferred to a vessel for distillation was distilled under reduced pressure to remove unreacted α-methylstyrene. The residue after distillation was cooled and added to a separatory funnel of 1-liter capacity containing 250 ml of water followed by the addition of 300 ml of ether. The separatory funnel was shaken and the aqueous layer was discharged therefrom. The etheric solution was further washed twice each time with 250 ml of water and dried with anhydrous magnesium sulfate. After distilling off the ether, the reaction mixture was subjected to distillation under reduced pressure to give 65 g of a fraction boiling at 135 to 137° C. under a pressure of 0.2 mmHg which was identified to be 1,4-dimethyl-4-phenyl-1,2,3,4-tetrahydronaphthalene having a purity of 96%. The above mentioned yield was 11% of the theoretical value. The identification of this compound was performed by the gas chromatography-mass spectrometric analysis, NMR spectrometric analysis and infrared absorption spectrophotometry.

EXAMPLE 1

Into a stainless steel-made autoclave of 1-liter capacity equipped with an electromagnetic stirrer were introduced 59.1 g (0.25 mole) of 1,4-dimethyl-4-phenyl-1,2,3,4-tetrahydronaphthalene obtained in the above described Preparation, 200 ml of methylcyclohexane and 3 g of a ruthenium catalyst containing 5% by weight of ruthenium supported on a powdery carbon carrier (a product by Nippon Engelhardt Co.) and the hydrogenation was performed at 150° C. for 2 hours under a hydrogen pressure of 20 atmospheres. After completion of the reaction, the catalyst was separated from the reaction mixture by filtration and washed with 50 ml of methylcyclohexane to give a washing which was combined with the filtrate of the reaction mixture. The reaction mixture was then freed of methylcyclohexane by evaporation in a rotary evaporator to give 58.9 g of a final product which was identified to be 1-cyclohexyl-1,4-dimethyl decahydronaphthalene by the elementary analysis, gas chromatography-mass spectrometric analysis, NMR spectrometric analysis and infrared absorption spectrophotometry. The above mentioned yield was 98% of the theoretical value. The results of the analyses are shown below.

Figure 2:
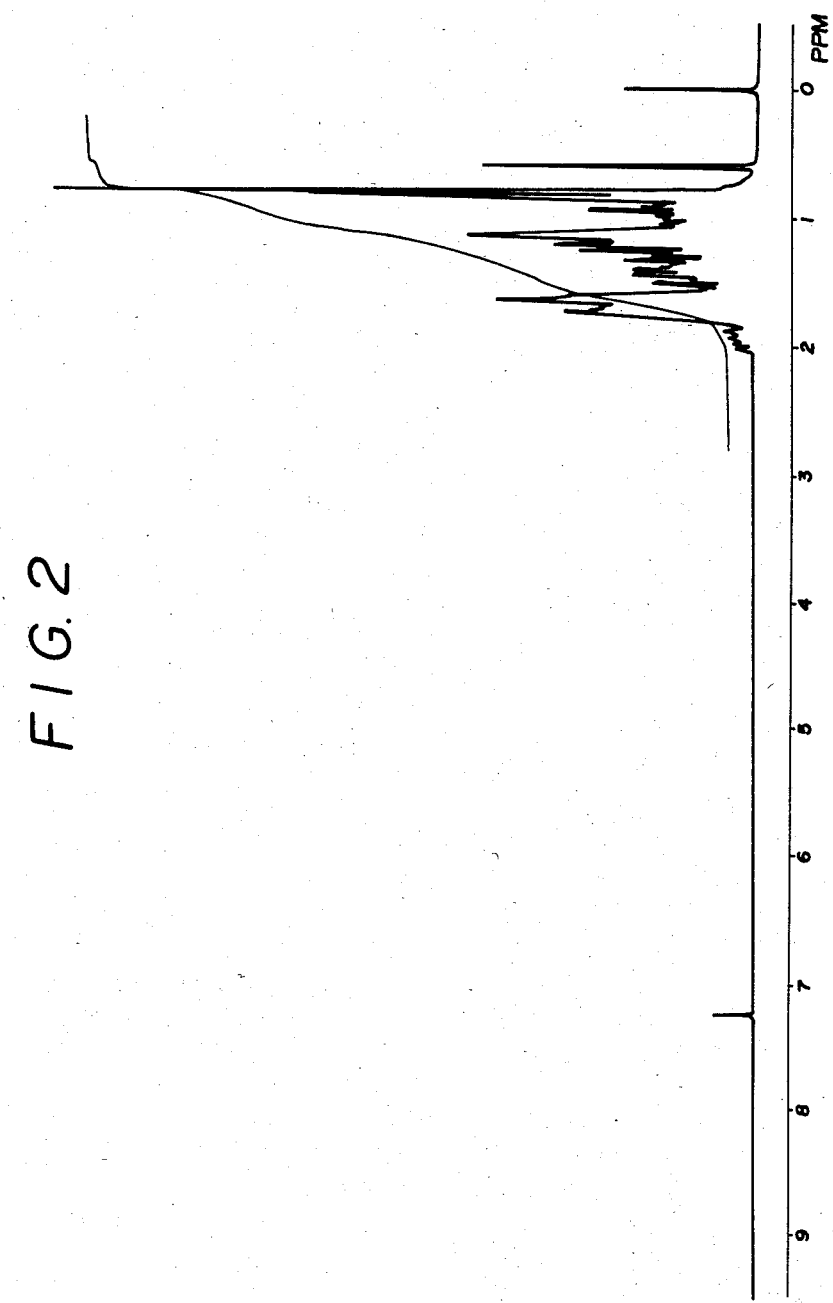
FIG. 2 is a proton nuclear magnetic resonance (NMR) spectrum of the same compound.
Figure 3:
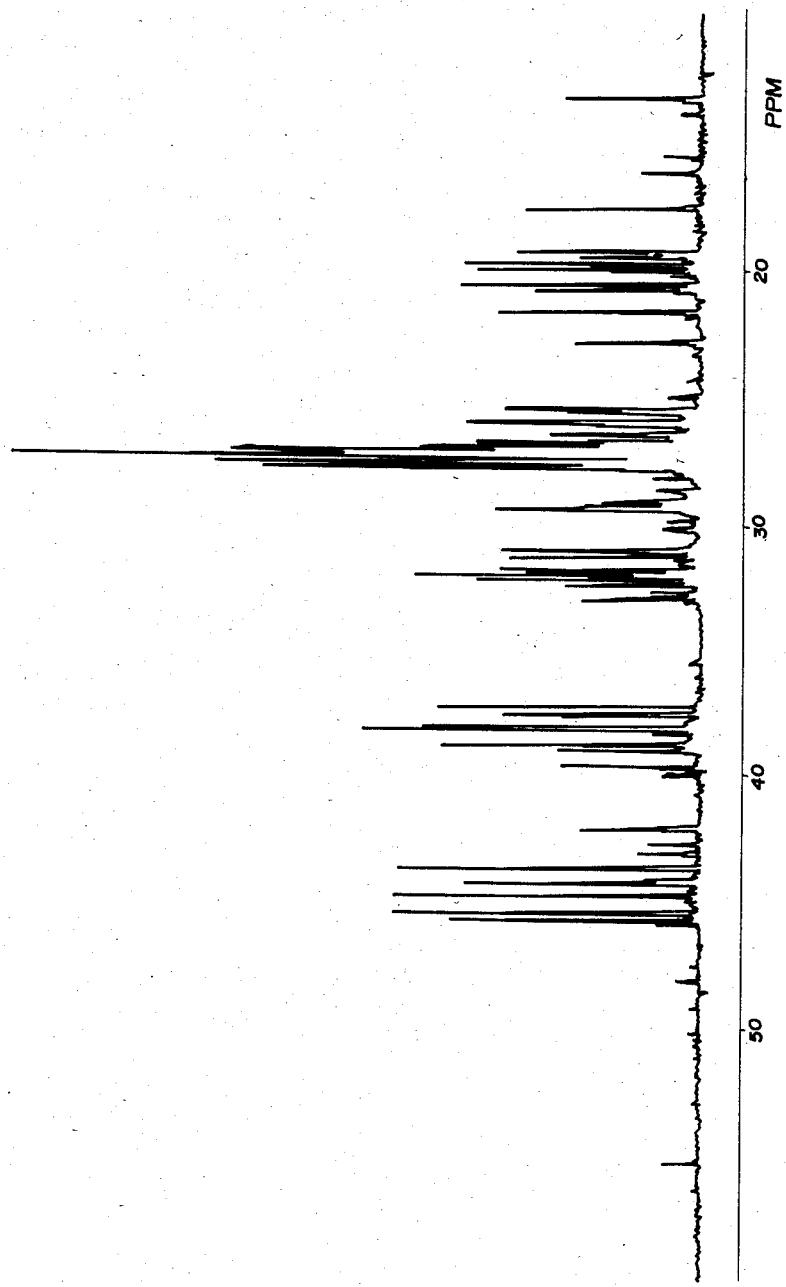
FIG. 3 is a $^{13}C$ NMR spectrum of the same compound.

(1) Elementary analysis:
Found, %: C 87.2; and H 12.8.
Calculated as $C_{18}H_{32}$, %: C 87.0; and H 13.0.
(2) Refractive index: $n_d^{20} = 1.5112$
(3) Specific gravity: $d_4^{15} = 0.9512$
(4) Infrared absorption spectrum: see FIG. 1 (taken with an infrared spectrophotometer Model A-2 manufactured by Nippon Bunko Co.).
(5) Proton NMR spectrum: see FIG. 2 (taken with a NMR spectrometer Model GX-270 manufactured by Nippon Denshi Co.).
(6) $^{13}C$ NMR spectrum: see FIG. 3 (taken with the same instrument as above).

EXAMPLE 2

The compound prepared in Example 1 was subjected to the measurement of the traction coefficient to give values of 0.074° at 120° C. and 0.066° at 140° C.

The measurement of the traction coefficient was undertaken using a two roller machine. Namely, two rollers of the same size each having a diameter of 60 mm and a height of 6 mm were contacted with each other under a contacting pressure of 140 kg given by a spring and one of them was rotated at a constant velocity of 2000 rpm while the other was rotated at a lower but constant velocity of 1700 rpm. The torque was determined by use of a strain gage and a torque meter, from which the traction coefficient was calculated. The rollers were made of a carbon steel SCM-3 and the surfaces thereof were finished to have a surface roughness of $R_{max} = 0.2$ μm by buffing using an alumina abrasive of 0.03 μm particle diameter. The Herzian contact pressure was 75 kg/mm². The measurements were performed under control of the temperature of the oil in the oil reservoir which could be heated by means of a heater.

COMPARATIVE EXAMPLE 1

Into a glass-made flask of 3-liter capacity were introduced 1000 g of α-methylstyrene, 50 g of acid clay and 50 g of ethylene glycol and the mixture was agitated at 140° C. for 2 hours to effect the reaction. After completion of the reaction, the reaction mixture was filtered to remove the acid caly as the catalyst and the filtrate was subjected to distillation to give 900 g of a fraction boiling at 125° to 130° C. under a pressure of 0.2 mmHg after stripping of the unreacted α-methylstyrene and ethylene glycol. The thus obtained fraction was identified to be a mixture of 95% by weight and 5% by weight of a linear dimer and a cyclic dimer, respectively, of α-methylstyrene from the results of the NMR and gas chromatographic analyses.

The fraction was subjected to a post-treatment of hydrogenation in the same manner as in Example 1 to give a fluid for traction drive mainly composed of 2,4-dicyclohexyl-2-methyl pentane. The fluid had a specific gravity $4^{15}$ of 0.90, kinematic viscosity of 22 cSt at 40° C. and 3.7 cSt at 100° C. and viscosity index of 16.

The fluid was further subjected to the determination of the traction coefficient in the same manner as in Example 2 to give values of 0.070 and 0.059 at temperatures of 120° C. and 140° C., respectively. This result indicates that the traction coefficient of the fluid prepared in this comparative example 1 is definitely lower than that of the inventive compounds despite the same starting material of α-methylstyrene used in the preparation of them.

What is claimed is:

1. 1-Cyclohexyl-1,4-dimethyl decahydronaphthalene expressed by the structural formula

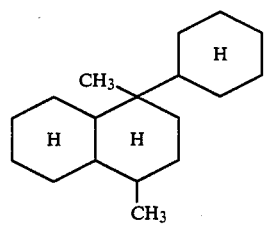

2. A fluid for traction drive which comprises 1-cyclohexyl-1,4-dimethyl decahydronaphthalene expressed by the structural formula

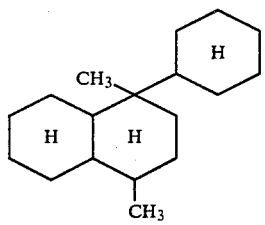

3. A process for improving the coefficient of traction between at least two relatively rotatable elements in a torque transmitting relationship and for maintaining said coefficient of traction at a high level at operating temperatures up to 120°–140° C. which comprises introducing between the tractive surfaces of said elements a traction drive fluid which comprises 1cyclohexyl-1,4-dimethyl decahydronaphthalene expressed by the structural formula

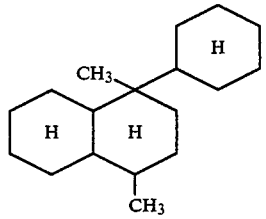

* * * * *